(12) United States Patent
Appeldoorn et al.

(10) Patent No.: US 7,304,039 B2
(45) Date of Patent: Dec. 4, 2007

(54) GLUCOSE-BASED COMPOUNDS WITH AFFINITY TO P-SELECTIN

(75) Inventors: Chantal Catharina Maria Appeldoorn, Leiden (NL); Erik Anna Leonardus Biessen, Leiden (NL); Thomas Jacobus Maria Molenaar, Leiden (NL); Theodorus Josephus Cornelis Van Berkel, Haarlem (NL)

(73) Assignee: Astellas Pharma Europe B.V., Leiderdorp (NL)

( * ) Notice: Subject to any disclaimer, the term of this patent is extended or adjusted under 35 U.S.C. 154(b) by 28 days.

(21) Appl. No.: 10/530,601

(22) PCT Filed: Oct. 13, 2003

(86) PCT No.: PCT/EP03/11457

§ 371 (c)(1),
(2), (4) Date: Apr. 7, 2005

(87) PCT Pub. No.: WO2004/033473

PCT Pub. Date: Apr. 22, 2004

(65) Prior Publication Data

US 2005/0261207 A1 Nov. 24, 2005

(30) Foreign Application Priority Data

Oct. 11, 2002 (EP) .................................. 02079232

(51) Int. Cl.
*A61K 31/70* (2006.01)
*A61K 31/715* (2006.01)
*A61K 9/127* (2006.01)

(52) U.S. Cl. .......................... 514/23; 514/25; 514/559; 514/460; 514/54; 435/105; 536/1.11; 536/4.1

(58) Field of Classification Search ................. 514/25, 514/459, 23; 435/105
See application file for complete search history.

(56) References Cited

U.S. PATENT DOCUMENTS 5,604,207 A * 2/1997 DeFrees et al. ............... 514/25
5,830,871 A * 11/1998 Wong et al. .................. 514/23
5,916,876 A 6/1999 Heavner et al.

OTHER PUBLICATIONS

Wong, C-H; J.Am. Chem. Soc. 1997, 119, 8152-8158.*
Lin et al., "Synthesis of Sialyl Lewis X Mimetics as Selectin Inhibitors by Enzymic Aldol Condensation Reactions", *Bioorganic & Medicinal Chemistry*, vol. 7, No. 3, 1999, p. 427.
Weitz-Schmidt et al., "Selectin/Glycoconjugate Binding Assays for the Identification and Optimization of Selectin Antagonists", *Analytical Biochemistry*, vol. 273, No. 1, 1999, pp. 81-88.

* cited by examiner

*Primary Examiner*—Shaojia Anna Jiang
*Assistant Examiner*—Roy P. Issac
(74) *Attorney, Agent, or Firm*—McDonnell Boehnen Hulbert & Berghoff LLP

(57) ABSTRACT

The present invention relates to certain glucose-based compounds that have an affinity to P-selectin. Further, the invention relates to the use of these glucose-based compounds for the preparation of pharmaceutical compositions for the treatment of disorders associated with P-selectin, to conjugates, pharmaceutical carriers and drug delivery systems comprising said compounds, and to a method for determining whether a compound is capable of binding to P-selectin.

13 Claims, 3 Drawing Sheets

2

3

6d

6f

6i

Reagents: (a) allyl alcohol, camphersulfonic acid; (b) Ac₂O, pyr; (c) OsO₄, NMO; (d) NaIO₄; (e) DHAP, FruA; (f) NaOMe.

Conditions: (a) Troc-Cl; (b) allyl alcohol, camphersulfonic acid; (c) Ac₂O, pyridine; (d) zinc, AcOH; (e) R¹-Cl; (f) OsO₄, NMO; (g) NaIO₄; (h) DHAP, FruA; (i) NaOMe.

| Compound | R¹ | Compound | R¹ |
|---|---|---|---|
| c | nonanoyl | g | 4-nitrobenzoyl |
| d | 2,2,2-trichloroethoxycarbonylmethyl (acetate) | h | 4-(trifluoromethyl)benzoyl |
| f | benzoyl | i | 2-naphthoyl |

# GLUCOSE-BASED COMPOUNDS WITH AFFINITY TO P-SELECTIN

The present invention relates to sugar-derived compounds which selectively bind to the adhesion molecule human P-selectin, to the use of such compounds for the preparation of pharmaceutical compositions for the treatment of P-selectin associated disorders, to conjugates, pharmaceutical carriers and drug delivery systems comprising said compounds, and to a method for determining whether a compound is capable of binding to P-selectin.

BACKGROUND OF THE INVENTION

In recent years, cell surface adhesion molecules have become recognized as key mediators in numerous cellular processes including cell growth, differentiation, immune cell transmigration and response and cancer metastasis.

Four major categories of adhesion molecules have been identified: the immunoglobulin superfamily cell adhesion molecules (CAMs), cadherins, integrins and selectins.

The selectins represent a family of presently three transmembraneous, carbohydrate-binding glycoproteins: "endothelial" E-selectin, "leukocyte" L-selectin, and "platelet" P-selectin. All three selectins are divalent cation (e.g. calcium) dependent and possess an extracellular domain with a carbohydrate recognition motif, an epidermal growth factor-like motif and some smaller domains related to complement-regulatory proteins.

Human P-selectin (also referred to as GMP-140, LECAM-3, PADGEM, CD62 and CD62P) is expressed by platelets and endothelial cells. When expressed on the surfaces of these cells, its most notable effect is the slowing of leukocytes as these leave the capillaries and enter the postcapillary venules, the latter representing the major site of leukocyte-endothelium adhesion. The slowing process is observed as leukocyte rolling, signifying an initial adhesion with relatively low affinity. The firm adhesion of rolling leukocytes is primarily mediated by integrins.

In endothelial cells P-selectin is stored on Weibel-Palade bodies; in platelets it is found in the α-granules. Following activation, P-selectin is mobilized to the cell surfaces within a few minutes in response to a variety of inflammatory or thrombogenic agents. The endothelial P-selectin's primary function is to recruit leukocytes into postcapillary venules, while platelet P-selectin also results in the formation of thrombi. One of the presently known natural ligands of P-selectin is PSGL-1 (P-selectin glycoprotein ligand-1), a 120 kDa sialoprotein expressed on the surface of leukocytes where it is concentrated at the uropod. More detailed descriptions of the structure and functions of P-selectin are found in numerous publications (e.g. J. Panes, Pathophysiology 5: 271 (1999); F. Chamoun et al., Frontiers in Bioscience 5: e103 (Nov. 1, 2000) and S.-I. Hayachi, Circulation 102: 1710 (2000)).

Inflammation and inflammatory processes play a major role in the pathophysiology of numerous diseases and conditions. Conditions of the brain in which increased selectin levels were found, and which may therefore involve selectin-mediated pathophysiological events, include severe traumatic brain injury, relapsing-remitting multiple sclerosis, cerebral artery occlusion, ischemia and stroke. Conditions of the heart in which selectins are suggested to play a role include acute myocardial infarct, arterial injury, such as produced by angioplasty, and ischemia. Similarly, selectins are involved in conditions of the kidneys, such as renal injury from ischemia and reperfusion, and renal failure. Furthermore, selectins appear to play a role in organ transplant rejection, cold ischemia, hemorrhagic shock, septic shock, tumor metastasis, chronic inflammation, rheumatoid arthritis, inflammatory bowel disease, atherosclerosis, restenosis, angiogenesis, disseminated intravascular coagulation, adult respiratory stress syndrome and circulatory shock.

Thus, it would seem feasible to improve these and other conditions involving the activation of endothelial cells and leukocytes and specifically the mobilization and expression of P-selectin by specifically interrupting the P-selectin cascades. This can be done, for instance, by the administration of ligands which selectively bind to human P-selectin, but which do not possess its bioactivity. By this method mobilised P-selectin could be inactivated and leukocyte-induced tissue damage prevented. Potentially, the same effect could be achieved by gene therapy, provided the P-selectin ligand or antagonist is a peptide or modified peptide. According to this method somatic cells of a person in need of the therapy would be transfected with an expression vector carrying a DNA sequence encoding a P-selectin antagonist.

P-selectin ligands or antagonists may also be used for the prevention of diseases and conditions described above. Furthermore, such ligands may also be useful in the in vivo or in vitro diagnosis of these diseases.

Various attempts have been made in recent years to identify or create such selective ligands to P-selectin. So far, a number of substances were tested, but no clinical studies have yet provided conclusive evidence that any of these compounds produce the desired clinical effects while being tolerable in terms of side effects.

For instance, antibodies to P-selectin, that were produced and tested in animal models, were found to protect kidneys from ischemic-reperfusion injury (H. C. Rabb et al., JASN 5: 907, 1997; U.S. Pat. No. 6,033,667). In another study a recombinant soluble form of P-selectin glycoprotein ligand-1 (rPSGL-Ig) was used to inhibit thrombosis in cats (M. J. Eppihimer et al., Arteriosclerosis, Thrombosis, and Vascular Biology 20: 2483, 2000). WO-A-99/41363 discloses podocalyxin-like proteins that bind to selectins. WO-A-00/41711 describes various smaller peptides or peptide sequences that bind to members of the human selectin family; most of the sequences comprise one or more units of leucine or isoleucine.

As another approach to inhibit the P-selectin cascade various peptides derived from the lectin domain of the selectin family were found to inhibit neutrophil adhesion to P-selectin (e.g. U.S. Pat. No. 6,111,065 and U.S. Pat. No. 5,916,876); these peptides probably bind to P-selectin receptors on leukocytes.

In WO-A-94/05269 peptides are described which inhibit binding of selectins such as P-selectin, E-selectin and L-selectin. These peptides have as their core region portions of the 11-18 amino acid sequence of P-selectin, E-selectin or L-selectin. Further, WO-A-95/31210 relates to peptides and compounds that bind selectins including endothelium leukocyte adhesion molecule 1 (ELAM-1). These peptides are used for blocking adhesion of leukocytes to the selectins, i.e. especially E-selectin, but also P-selectin or L-selectin, for the purpose of inhibiting inflammation.

In Applicant's non pre-published patent application WO 03/020753 and pending international application PCT/EP03/07260 novel compounds are described with peptidic core regions and certain consensus motifs which are essential for recognising P-selectin. In contrast to most other known substances, which have an affinity to the selectins, these compounds possess a high degree of P-selectin specificity.

Little is yet known about the stability of these compounds in vitro and in vivo, and—as in the case of most therapeutic or diagnostic peptides—in order to become effective it is mandatory that these compounds are injected. Most patients, however, prefer non-parenteral routes of administration, especially for chronic therapies.

Apart from the peptide approach the fact, that the selectins recognize sialyl Lewis sugar X (sLeX), has also led to a number of efforts towards the development of sugar-based ligands having selectin-binding activity. For example, U.S. Pat. No. 5,750,508 discloses synthetical ligands based on fucose and sialic acid, wherein the fucose and sialic acid moieties are separated by non-carbohydrate linkers. WO-A-96/09309 discloses oligosaccharide structures that are potential ligands to E- and P-selectin. WO-A-98/06730 describes modified oligosaccharides which are derivatives of sLeX, in which the neuraminic acid residue and the N-acetylglucosamine monomer have been replaced by various substituents. U.S. Pat. No. 5,830,871 discloses sugar-based selectin inhibitors and sLeX mimetics which can be prepared by an aldol addition reaction between a glycoside aldehyde precursor and dihydroxyacetone phosphate or a derivative thereof. However, these compounds do not have much selectivity for P-selectin.

Thus there is a need for substances with selective affinity to P-selectin, which can be used for preparing pharmaceutical compositions for the diagnosis, prevention and treatment of various diseases and conditions involving the adherence of leukocytes to vascular endothelial cells or to platelets. There is also a need for P-selectin ligands, which can be used as targeting molecules or moieties in pharmaceutical compositions for the targeting of drugs or genetic material to tissues expressing P-selectin. Furthermore, there is a need for compositions comprising said substances in a form suitable to be used in a more patient friendly way than by parenteral application.

SUMMARY OF THE INVENTION

It is an object of the invention to provide compounds with affinity to human P-selectin.

In particular, it is an object of the invention to provide compounds which act as antagonists or partial antagonists of P-selectin.

It is another object of the invention to provide compounds which act as targeting ligands with an ability to target drugs and genetic material to cells and tissues expressing P-selectin.

Yet another object is the presentation of uses of such compounds and of compositions which contain the compounds.

Other objects of the present invention will become clear on the basis of the following description.

LEGENDS TO THE FIGURES

DETAILED DESCRIPTION OF THE INVENTION

Figure 1:
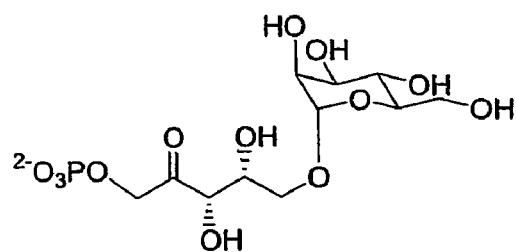
FIG. 1 depicts the structural formula of reference compound 2 and some preferred compounds in accordance with the present invention.
Figure 1:
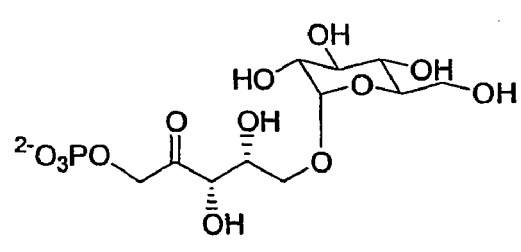
Figure 1:
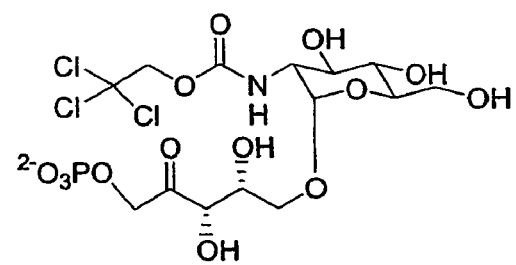
Figure 1:
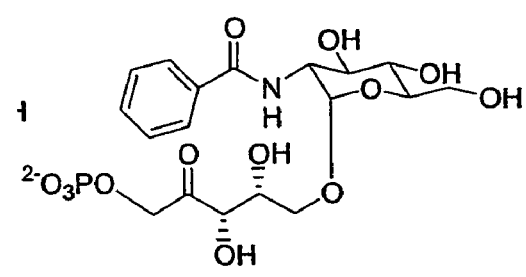
Figure 1:
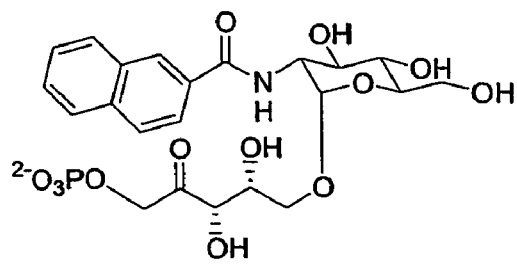

The present inventors have discovered that glucose-based sLeX mimetics are particularly useful for the selective binding to P-selectin. Unlike E- and L-selectin, P-selectin binding does not require an axially orientated hydroxyl group at the C-2 position of the monosaccharide.

According to the invention, glucose-based compounds are provided, having both affinity to and selectivity for P-selectin and having the potential to be powerful modulators or antagonists of P-selectin, which compounds are represented by the following formula Ia:

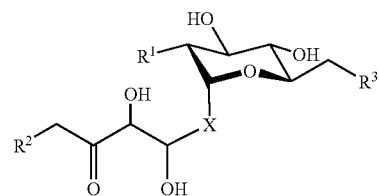

and their stereo-isomers represented by the following formula Ib:

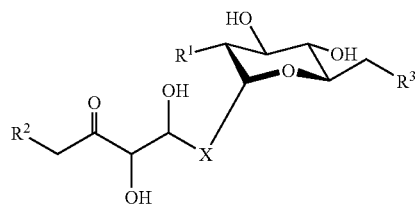

wherein:

X is an optional group, which represents —O—, —OCH$_2$—, —S—, —SCH$_2$—, —NH— or —NHCH$_2$—, preferably X is not present or represents —O—;

R$^1$ represents QR$^4$, wherein Q represents —O—, —NH—, —NH—(C=O)—, —O—(C=O), —NH—(C=O)—O or —NH—(C=O)—NH— and wherein R$^4$ represents H, an alkyl moiety, an aromatic moiety or a group comprising an electron withdrawing moiety, R$^2$ is a moiety bearing at least one negative charge and R$^3$ can be any group, provided that if Q is —O— and R$^4$ is H, X is present.

The compounds of the invention are further characterized by a 4-oxo-2,3-dihydroxy-n-pentylene group, optionally coupled through a linker group at the C-1 position of the monosaccharide template. This group is further modified by a negatively charged substituent R$^2$ at its C-5 position. With the term "negatively charged substituent", it is meant a substituent that has a negative charge under physiological compositions. Among the preferred negatively charged substituents are substituents comprising a phosphate group, a phosphonate group, a carboxylate, a sulphonate. Particularly preferred is a phosphate group.

The 4-oxo-2,3-dihydroxy-n-pentyl group is attached to the C-1 position of the monosaccharide ringstructure, either directly, which is a preferred option, or through an oxygen atom, an OCH$_2$ group, a sulphur atom, an SCH$_2$ group, an NH group or an NHCH$_2$ group, but preferably through an oxygen atom. The two preferred options represent the fact that the compounds can be derivatives of C-glucosides or O-glucosides. See in this respect the following reaction scheme:

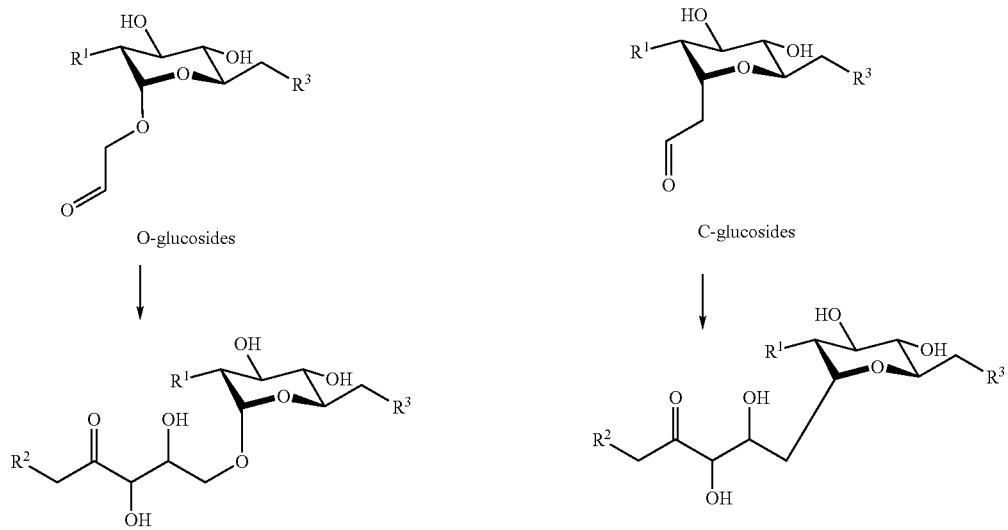

O-glucosides          C-glucosides

Without wishing to be limited by any theoretical consideration, it is hypothesized that the compounds of the present invention have a strong interaction with P-selection because the 4-oxo-2,3-dihydroxy-n-pentyl group mimics the two hydroxyl functions of the galactose moiety and the carboxylic acid function of the N-acetylneuraminic acid within the natural ligand sialyl Lewis X (sLeX).

At the C-6 position of the monosaccharide structure, the compounds have a substituent which is herein defined as $R^3$. In general, $R^3$ may represent any substituent, inclusive of a hydrogen atom. In fact, $R^3$ is the substituent required for the functionalisation. It is not particularly critical what kind of group is present. The group may be a hydroxyl, an amine, an azide, an aldehyde or a carboxylic acid or a derivative thereof. In one of the preferred embodiments of the invention, $R^3$ is hydroxyl, which is the group originally present at the C-6 position in the glucose molecule which serves as a monosaccharide template of the compounds. In another preferred embodiment $R_3$ represents an —$YR^5$ moiety, wherein Y is preferably —O—, —$CH_2$—, or NH and most preferably —O— and wherein $R^5$ comprises at least one carbon atom. Preferred groups $R^5$ are linear or branched alkyl or aryl groups, linear or branched aralkyl or alkaryl groups, which groups can contain one or more heteroatoms, such as nitrogen, oxygen, phosphorous, sulphur atoms; the groups can be substituted with halogen atoms, hydroxyl groups, oxygen atoms, alkoxy and aryloxy groups, amino or substituted amino groups, as well as other substituents. Instead of through a linker Y, the group $R^5$ can also be coupled directly to the saccharide template.

Furthermore, the C-6 position is one of the preferred reactive positions where the core structure of the compounds can be coupled to other functional moieties, such as spacers or anchoring moieties. Directly or indirectly via a spacer, the C-6 can be coupled to another active compound which is not derived from a compound of the invention to form a drug conjugate, or it can be coupled to an anchoring moiety which is capable of anchoring the compound to a colloidal or microparticulate drug carrier, such as a liposome, a niosome, a nanodroplet, a nanoparticle, a nanocapsule, a nanosphere, a microparticle, a dendrimer, a microcapsule, a microsphere, a colloidal complex, a micelle, a mixed micelle, a cross-linked micelle, a viral vector, or a lipid complex. As used herein, the anchoring capability comprises both covalent and non-covalent interactions between the anchor moiety and the substrate, i.e. the colloidal or microparticulate drug carrier, by which the compound may be linked to the substrate.

However, a compound of the invention can also be conjugated to another active compound or moiety (which is not derived from a compound according to the present invention) or to an anchoring moiety via a different type of linkage, e.g. at the C-2 position of the monosaccharide structure. In this way, the compound of the invention can be used as a targeting means to direct the other active compound or the colloidal or microparticulate drug carrier to cells and tissues expressing P-selectin. Thus it is possible to deliver another active compound specifically to such cells and tissues, regardless of the type of activity or mechanism of action of the other active compound.

In a further embodiment, a compound of the invention is coupled to one or more other compounds or moieties which also bind to P-selectin. For instance, in Applicant's non pre-published patent application WO 03/020753 and pending international patent application PCT/EP03/07260 compounds with peptidic core regions and certain consensus motifs recognising P-selectin are disclosed, which compounds can be used in this embodiment. For this purpose, these compounds are incorporated by reference in the present description. Conjugates or colloidal or microparticulate drug carriers comprising at least one compound of the present and at least one peptidic compound with affinity to P-selectin may be particularly useful to provide a high degree of P-selectin binding. This may be assumed because the compounds bind to different sites of the P-selectin molecule: while the peptides have affinity to a non-active binding site, the sugar ligands of the present invention appear to bind to the active site of P-selectin.

The compounds of the invention are further characterised in that they possess a substituent $R^1$ at the C-2 of the monosaccharide structure. This substituent $R^1$ is much more critical than substituent $R^3$. Without wishing to be bound by any theory, it is believed that $R^1$ plays an active role in the recognition of or selectivity to P-selectin. $R^1$ represents $QR^4$, wherein Q represents —O—, —NH—, —NH—(C═O)—, —O—(C═O), —NH—(C═O)—O— or —NH—(C═O)—NH and preferably —NH—(C═O)—; and wherein $R^4$ represents any substituent comprising at least one carbon atom. Preferred groups $R^4$ are linear or branched alkyl or aryl groups, linear or branched aralkyl or alkaryl groups, which groups can contain one or more heteroatoms, such as nitrogen, oxygen, phosphorous, sulphur atoms, and which groups preferably have up to 20 carbon atoms, more preferably between 1 and 12 carbon atoms; the groups can be substituted with halogen atoms, hydroxyl groups, oxygen atoms, alkoxy and aryloxy groups, amino or substituted amino groups, as well as other substituents. In especially preferred embodiments, the electron withdrawing groups are present on the aromatic moieties.

Most preferably $R^4$ is H, an alkyl moiety, an aromatic moiety or an electron withdrawing moiety.

The aromatic moiety can, for example, be a phenyl, naphthyl, cresyl, tolyl, anthracyl, phenanthryl, pyridyl, pyrazyl, pyridazyl or quinolyl group, which group can optionally be substituted. Preferably, $R^4$ is a phenyl or naphthyl group.

In another embodiment, $R^4$ is a group comprising an electron-withdrawing moiety. Preferably, the electron withdrawing moiety is a moiety selected from the group consisting of nitro, —(C=O)-alkyl, cyanonitrile, —SO$_3$H, CCl$_3$ or CF$_3$; more preferably, the electron withdrawing group is a nitro group.

The selection of the group $R^4$ was found to have a significant influence on the P-selectin binding activity of a compound of the invention. Depending on the substituent $R^4$, the affinity to P-selectin can actually be increased to reach a several-fold higher affinity than the endogenous ligand sLeX. Surprisingly, it was found that substituents comprising aromatic groups are particularly useful. For instance, the selection of phenyl or naphthalene for $R^4$ led to compounds with particularly high affinity and selectivity for P-selectin. Without wishing to be bound by any theory, it is assumed that, in the position of $R^4$, a substituent that is capable of participating in a π-π interaction may actually be able to bind to a tyrosine group (Tyr$^{94}$) which is present in P-selectin, and which was previously found to be in close proximity to the C-4 hydroxyl group of the galactose moiety of sLeX bound to the CRD domain of P-selectin (Somers et al., Cell, 103, 467-479, 2000). $R^4$ hence preferably is a substituent able to participate in a π-π interaction with a tyrosine group, and more preferably represents a phenyl of naphthalene group.

Compounds of the invention can be prepared by various different routes of synthesis. Depending on the particular selection of substituents as discussed above, the most useful reaction schemes may differ from each other. In one of the preferred routes of synthesis, glucose is used as a starting material to prepare an O-allyl glucopyranoside by Fischer synthesis, which may be followed by the acetylation and oxidation to form glycosyl aldehydes. These aldehydes are subsequently linked to a dihydroxyacetone derivative through an aldolase-catalyzed reaction.

For the condensation of the glycosyl aldehyde to a dihydroxyacetone phosphate, various types of aldolase can be used as enzymatic catalysts, including D-fructose-1,6-diphosphate aldolase from rabbit muscle (RAMA) and fructose diphosphate aldolase from *St. carnosus* (FruA). As RAMA combines a relatively poor stability in organic solvents with a high substrate specificity, its tolerance to aldehyde acceptors is quite low. In view of its superior solvent stability and substrate specificity, it is therefore recommended to use FruA, which considerably extends the range of conditions and substrates of aldolase catalyzed condensation reactions to be used in organic synthesis. Ilustratively, condensation proceeded smoothly even when fully acetylated glycosyl aldehydes and dihydroxyacetone phosphate (DHAP) are used as substrates in a mixture of an organic solvent such as tetrahydrofuran (THF) or dimethylsulfoxide (DMSO) with water.

In order to introduce selected substituents represented by $R^1$, again several synthetic pathways can be followed. For instance, if Q is selected to be —NH—(C=O)—, a glucosamine can be used as staring marterial. The glucosamine can be converted into the 2,2,2-trichloroethoxycarbonyl (Troc) derivative under Schotten-Baumann conditions and subsequently allylated and acetylated to yield the O-allyl glycoside. After removing the Troc group, the free amino function can be acylated with the respective acyl chlorides.

Salts, adducts, solvates and other derivatives of the compounds as defined above are also within the scope of the invention. In a preferred embodiment, the compound of the invention is in the form of a salt which has been formed by the addition of an acceptable base. However, acid addition salts may also be feasible. Whether an acid or a base is pharmaceutically acceptable can be easily determined by a person skilled in the art taking into consideration the specific intended use. For instance, not all acids and bases that are acceptable for in vitro diagnostic compositions can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates are encompassed.

A further aspect of the invention refers to the uses of the disclosed compounds. Since the compounds bind selectively to P-selectin, they can, depending on their type of interaction with P-selectin after binding, function as antagonists, partial antagonists, or as targeting means to target conjugated substances or drug carrier systems such as liposomes or nanoparticles to cells and tissues expressing P-selectin. Thus, the compounds can be advantageously used in pharmaceutical compositions. According to the invention, such pharmaceutical compositions are provided as well.

As used herein, the term "pharmaceutical composition" refers to therapeutic and diagnostic compositions, as well as to medicaments and diagnostics containing such compositions. Therapeutic compositions and medicaments are used for the prevention, inhibition, reduction or treatment of diseases and other conditions of mammals of which conditions improvement is desired. Diagnostics and diagnostic compositions are used for the diagnosis of such diseases in vivo and in vitro.

A preferred use of the compounds is for preparing therapeutic compositions or medicaments, especially for diseases or discomforts or other conditions involving the activation or overexpression of P-selectin, such as therapeutic compositions or medimants to prevent or improve diseases and conditions involving the adhesion of leukocytes, such as monocytes and neutrophils, to the vascular endothelium and to platelets. The compounds can also be used in compositions for treating diseases in which the inhibition of P-selectin-mediated intracellular signaling is desirable.

For instance, compositions containing one or more compounds of the invention can contribute to controlling leukocyte-mediated inflammatory processes. It is known that activated leukocytes release toxic molecules which can damage normal tissue. These inflammatory responses, some of which also involve P-selectin-mediated platelet activation, are part of several pathological conditions, such as (organ) transplant rejection, cold ischemia, hemorrhagic shock, septic shock, tumor metastasis, chronic inflammation, rheumatoid arthritis, inflammatory bowel disease, atherosclerosis, thrombosis, restenosis, angiogenesis, disseminated intravascular coagulation, adult respiratory stress syndrome, circulatory shock, severe traumatic brain injury, relapsing-remitting multiple sclerosis, cerebral artery occlusion, ischemia, stroke, acute myocardial infarct, arterial injury, such as produced by angioplasty, myocardial ischemia, renal injury from ischemia and reperfusion, and renal failure.

In another embodiment, the compounds are used in the preparation of diagnostic compositions or products. Such compositions can be used for in vitro tests to quantify P-selectin concentrations in body fluids as markers for the diseases and conditions described above. They may be also used for in vivo diagnostic imaging procedures to monitor P-selectin mediated atherosclerosis, aneurisms, restenosis following percutaneous transluminal coronary angioplasty (post-PTCA restenosis), and other conditions selected from those in which P-selectin is mobilized. As an option for this use, a compound according to the invention may be conjugated with a chelator, which is subsequently complexed with an isotropic label that is detectable by the chosen monitoring system.

Another use of the compounds is as a tool in research. Hence, the present invention also relates to a method for determining whether a compound is capable of binding to P-selectin or a functional equivalent of P-selectin, comprising contacting and incubating the compound to be tested and a predetermined amount of a compound according to the invention with a predetermined amount of P-selectin or said functional equivalent of P-selectin, and subsequently determining the amount of compound according to the invention.

More specifically, the compounds of the invention can be used to test the binding affinity of molecules to P-selectin or functional equivalents of P-selectin. To conduct this test method, P-selectin or a functional equivalent of P-selectin is contacted and incubated with a molecule to be tested for binding affinity and with a compound of the invention. A reduced binding of the compound of the invention would indicate an affinity of the molecule to P-selectin.

The compounds can also be used as targeting molecules or conjugates in pharmaceutical compositions for the targeting of drugs or genetic material to tissues that express P-selectin. As conjugates, the compounds can be directly coupled with active molecules or nucleic acids that are to be delivered to such tissues. Alternatively, they can be incorporated into or anchored onto the surface of liposomes or other lipid vesicles, emulsion droplets, polymers, micelles, nano- or microcapsules, nano- or microparticles to obtain targeted vehicles for drugs or genetic material which is delivered to P-selectin expressing tissues.

The pharmaceutical compositions preferably contain one or more compounds with P-selectin affinity as disclosed herein and at least one carrier or excipient. As used herein, a carrier or excipient is any pharmaceutically acceptable substance or mixture of substances having no substantial pharmacological activity, which can be used as a vehicle or as an auxiliary substance to formulate a compound into dosage form which is stable and easy to administer. Examples of pharmaceutically acceptable excipients are found in the monographs of all major pharmacopoeias.

In one embodiment, the composition is formulated and processed for parenteral injection, preferably for intravascular injection, such as intravenous or intra-arterial, but also for intramuscular, subcutaneous, intralesional, intraperitoneal or other routes of parenteral administration. The same principles that govern the formulation of other drugs for these administration routes will also teach those skilled in the art on how to prepare such compositions. For instance, one of the requirements of parenteral dosage forms is their sterility. Other requirements are described in all major pharmacopoeias, such as in USP 24, in the monograph "General Requirements for Tests and Assays. 1. Injections", p. 1775-1777. To increase the stability of a parenteral formulation, it may be necessary to provide a dried dosage form which must be reconstituted before it can be administered. An example of such a dosage form is a freeze-dried or lyophilized formulation.

It may be desirable to administer a compound of the invention as a parenteral controlled release dosage form to avoid frequent injections and to improve the effectiveness and convenience of the therapy. Various methods of preparing such depot formulations are known. Prolonged release may be provided by solid implants, nanoparticles, nanocapsules, microparticles, microcapsules, emulsions, suspensions, oily solutions, liposomes, or similar structures.

Excipients that are particularly useful for the preparation of parenteral formulations are solvents, cosolvents and liquid or semisolid carriers, such as sterile water, ethanol, glycerol, propylene glycol, polyethylene glycol, butanediol, fatty oils, short- and medium chain triglycerides, lecithin, polyoxyethylene castor oil derivatives; substances to adjust the osmolality and pH, such as sugars, especially glucose, sugar alcohols, especially mannitol, sodium chloride, sodium carbonate, citric acid, acetate, phosphate, phosphoric acid, hydrochloric acid, sodium hydroxide etc.; stabilizers, antioxidants, and preservatives, such as ascorbic acid, sodium sulfite or sodium hydrogen sulfite, EDTA, benzyl alcohol etc.; other excipients and lyophilization aids, such as albumin, dextran etc.

Alternatively, the pharmaceutical compositions may be designed for oral administration and processed accordingly. As a matter of fact, one of the particular advantages of the present invention over other known compounds binding to P-selectin, such as antibodies or peptides, is the fact that they have a higher potential to be stable in gastrointestinal fluids as they are not peptides. Appropriate oral dosage forms include tablets, hard capsules, soft capsules, powders, granules, orally disintegrating dosage forms, syrups, drops, suspensions, effervescent tablets, chewable tablets, oral films, lyophilized dosage forms, sustained release dosage forms, controlled release dosage forms. In one embodiment, the oral dosage form is an enterically coated solid dosage form to provide protection of the compound from the acidic environment of the stomach.

It may also be advantageous to administer a compound of the invention in a transmucosal dosage form. This route of administration is non-invasive and patient-friendly, at the same time it may lead to an improved bioavailability of the compound compared to oral administration, especially if the compound is not stable in the fluids of the digestive system, or if it is too large to be absorbed from the gut effectively. Transmucosal administration is possible via, for instance, nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form include one or more substances providing for mucoadhesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

The invention is further illustrated by the following examples which are not intended to define or limit the scope of the invention.

EXAMPLES

Example 1

Synthesis of Compound 3

Figure 2:
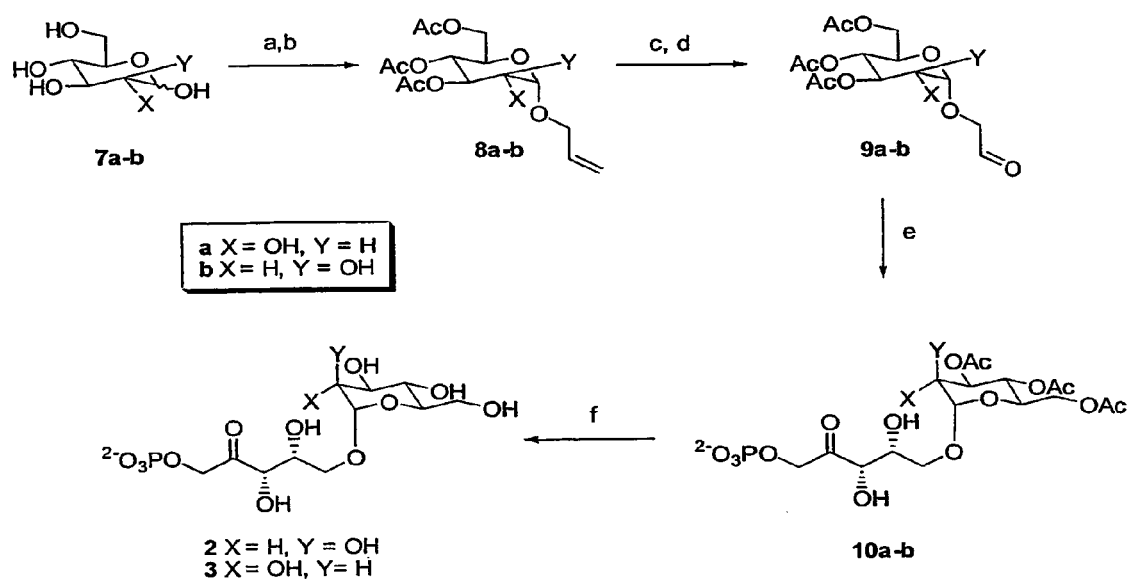
FIG. 2 shows the synthesis route for reference compound 2 and compound 3 according to the invention.

Glucose (compound 7a, see reaction scheme in FIG. 2) was converted into its O-allyl glucopyranoside through a Fischer synthesis in allyl alcohol in the presence of a catalytic amount of camphersulfonic acid. The crude mixture was acetylated to yield compound 8a. Compound 8a was oxidized to the corresponding diol by treatment with $OsO_4$ and N-methylmorpholin N-oxide monohydrate (NMO) in acetone/water and the diol was converted into aldehyde 9a using meta-sodium periodate. The desired α-isomer was obtained after purification by column chromatography. Compound 9a was subsequently linked to dihydroxyacetone phosphate by enzymatic catalysis with fructose diphosphate aldolase from *St. carnosus* (FruA) in a mixture of THF and water (1:3, v/v). Glycosyl phosphate 10a was obtained in good yield after incubation for approximately one day. Due to the presence of the protecting acetyl groups, purification of the product was greatly facilitated and involved flash chromatography. After purification, the acetyl groups were quantitatively removed by addition of a diluted NaOMe solution, resulting in the desired end product 3.

Compound 3: $^1$H NMR (MeOD): δ 4.75-4.70 (m, 1H), 4.55 (d, 1H, J=12.9 Hz), 4.36 (d, 1H), 3.80-3.55 (m, 8H).

Reference Example

Synthesis of Reference Compound 2

Reference compound 2 was prepared according to the same route as compound 3, starting from mannose (compound 7b) instead of glucose (compound 7a).

Compound 2: $^1$H NMR (MeOD): δ 4.81-4.73 (m, 1H), 4.67 (d, 1H, J=12.7 Hz), 4.55 (d, 1H, J=12.7 Hz), 3.85-3.81 (m, 2H), 3.73-3.66 (m, 2H), 3.63-3.46 (m, 3H).

Example 2

Binding of Compound 3 and Reference Compound 2 to P-Selectin

The activity of compound 3 was evaluated in an inhibition assay of $SO_3$-$sLe^a$-PAA-biotin binding to immobilized P-selectin as described in the literature (G. Weitz-Schmedt et al., Anal. Biochem. 238, 184-190, 1996) and compared to that of its mannosyl analogue (reference compound 2). A 96 microtiter plate (High binding flat bottom, Costar, Corning, U.S.A.) was coated overnight at 4° C. with 10 μg/ml goat anti-human IgG in coating buffer (50 mM $NaHCO_3$, pH 9.6). Subsequently, wells were washed with assay buffer (20 mM HEPES, 150 mM NaCl, 1 mM $CaCl_2$, pH 7.4) and incubated for 1 hour at 37° C. with blocking buffer (3% BSA in assay buffer). After washing with assay buffer, the wells were incubated for 2 hours at 37° C. with human P-selectin/IgG-Fc (0.3 μg/ml) or CD4/IgG-Fc (as negative control). Subsequently, wells were washed three times with assay buffer and incubated for 2 hours at 37° C. in binding buffer (0.1% BSA, 0.05% Tween 20 in assay buffer) with 0.33 μg/ml $HSO_3$-$Le^a$-PAA-biotin and the compound. The wells were washed six times with binding buffer and 3,3',5,5'-tetramethylbenzine (TMB)/$H_2O_2$ was added and incubated at room temperature for 15 minutes. The reaction was halted by addition of 2M $H_2SO_4$ and the absorbance was measured at 450 nm. As determined by this method, the $EC_{50}$ of glucosyl compound 3 for P-selectin was 2.0 mM and thus significantly lower than that of reference compound 2 (8.2 mM).

Example 3

Figure 3:
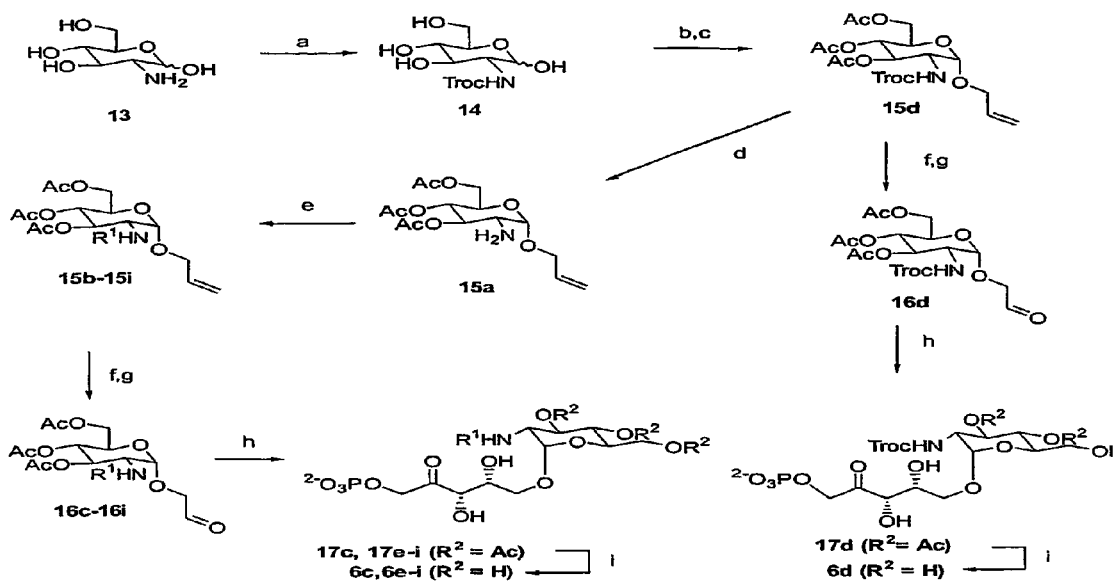
FIG. 3 shows the synthesis route for compounds 6c, 6d and 6f-6i according to the invention.

Synthesis of Compounds 6d, 6f and 6i (see FIG. 1 and Reaction Scheme in FIG. 3)

Glucosamine was converted into the 2,2,2-trichloroethoxycarbonyl (Troc) derivative 14 under Schotten-Baumann conditions (H. U. Bergmeyer, Methods of enzymatic analysis (1984), Verlag Chemie, Mannheim, Vol. IV p. 342-350). The crude product was allylated in allyl alcohol in the presence of camphersulfonic acid and subsequently acetylated to afford the α-oriented O-allyl glycoside 15d as major compound. The Troc-group was then removed by incubation with activated zinc in acetic acid, resulting in the intermediate amine 15a. Subsequently, free amine 15a was converted into the amides 15c and 15f-15i by addition of the cognate acid chloride under alkaline aqueous conditions. A variety of acid chlorides was chosen: octanoyl chloride (for 15c), 2,2,2-trichloroethoxycarbonylchloride (for 15d), benzoyl chloride (for 15f), nitrobenzyl chloride (for 15g), trifluoromethylbenzyl chloride (for 15h) and naphthoyl chloride (for 15i). The acylated compounds 15c, 15f-I and Troc-derivative 15d were then subjected to mild oxidation of the O-allyl group with $OsO_4$ and NMO and subsequently treatment with $NaIO_4$. The respective aldehydes were attained in good yield and condensed with DHAP under FruA catalysis as described in example 1 to attain the glucosyl phosphates 17c, 17d and 17f-i. The acetyl groups were then removed by treatment with 10 mM sodium methoxide solution and compounds 6c, 6d and 6f-i were isolated.

Compound 6c: $^1$H NMR (MeOD): δ 4.67 (d, 1H, J=13.1 Hz), 4.48 (d, 1H, J=12.8 Hz), 4.20 (d, 1H, J=5.8 Hz), 3.95-3.45 (m, 9H), 2.18-2.14 (m, 2H, C=OCH$_2$ octanoyl), 1.28 (s, 8H, 4×CH$_2$), 0.88 (m, 3H, CH$_3$).

Compound 6d: $^1$H NMR (MeOD): δ 5.03 (d, 1H, J=3.6 Hz, H-1), 4.70 (d, 1H, J=12.7 Hz), 4.53 (d, 1H, J=12.7 Hz), 4.23-4.11 (m, 2H), 3.93-3.85 (m, 3H), 3.77-3.63 (m, 5H), 3.48-3.42 (m, 2H).

Compound 6f: $^1$H NMR (MeOD): δ 7.87-7.41 (m, 5H, CH$_{arom}$), 4.98 (d, 1H, J=3.6 Hz), H-1), 4.69 (d, 1H, J=12.7 Hz), 4.51 (d, 1H, J=12.7 Hz), 4.15 (dd, 2H, J=10.8, 3.6 Hz), 3.86-3.63 (m, 7H), 3.42 (t, 1H, J=9.2 Hz).

Compound 6h: $^1$H NMR MeOD): δ 7.93 (d, 2H, J=8.1 Hz, CH$_{arom}$), 7.75 (d, 2H, J=8.2 Hz, CH$_{arom}$), 4.84-4.64 (m, 4H), 3.98-3.92 (m, 3H), 3.74-3.57 (m, 3H), 3.40-3.39 (m, 2H).

Compound 6i: $^1$H NMR (MeOD): δ 7.93-7.55 (m, 7H, CH$_{arom}$), 4.90-4.61 (m, 4H), 4.02-3.49 (m, 8H).

Example 4

Binding of Compounds 6d, 6f, and 6i to P-Selectin

The binding of compounds 6d, 6f, and 6i to P-selectin was evaluated using the same inhibition assay as described in example 2. The EC$_{50}$-values were found to be 4.5 mM for compound 6c, 3.7 mM for compound 6d, 0.90 mM for compound 6f and 0.32 mM for compound 6i. Compound 6h showed 36% inhibition at 5 mM.

The invention claimed is:

1. A compound having affinity to and/or selectivity for P-selectin and having structure of formula Ia:

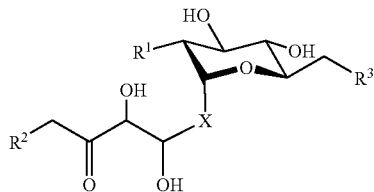

or a stereo-isomer thereof represented by the following formula Ib:

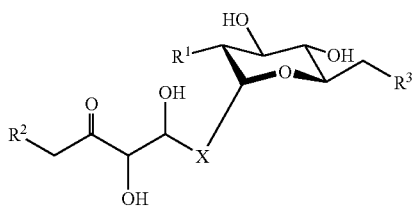

wherein:
X represents —O—, —OCH$_2$—, —CH$_2$—, —S—, —SCH$_2$—, —NH— or —NHCH$_2$—;
R$^1$ represents QR$^4$, wherein Q represent —O—, —NH—, —NH—(C=O)—, —O—(C=O), —NH—(C=O)—O— or —NH—(C=O )—NH—; and wherein R$^4$ represents a linear or branched alkyl or aryl group or a linear or branched aralkyl or alkaryl group;

R$^2$ is a phosphate, phosphonate, carboxylate, or sulphonate group; and
R$^3$ is OH or YR$^5$, wherein Y is —O—, —CH$_2$— or —NH— and R$_5$ is a linear or branched alkyl or aryl group or a linear or branched aralkyl or alkaryl group.

2. The compound according to claim 1, wherein X is —OCH$_2$—.

3. The compound according to claim 1, wherein Q represents —NH—(C=O)— or —NH—(C=O)—O—.

4. The compound according to claim 1, wherein R$^2$ is a phosphate group.

5. The compound according to claim 1, wherein R$^3$ represents OH.

6. The compound according to claim 1, wherein R$^4$ is substituted with a group selected from the group consisting of nitro, —C(O)alkyl, cyano, —SO$_3$H, —CCl$_3$, and —CF$_3$.

7. The compound according to claim 1, wherein R$^4$ is a phenyl or naphthalene group.

8. A composition comprising in a pharmaceutically acceptable carrier a compound according to claim 1 or a salt, or solvate thereof.

9. A method for determining whether a compound is capable of binding to P-selectin or a functional equivalent or P-selectin, comprising contacting and incubating the compound to be tested and a predetermined amount of a compound having affinity to and/or selectivity for P-selectin, represented by the formula Ia,

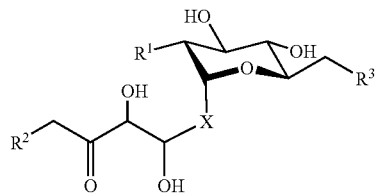

or a stereo-isomer thereof represented by the formula Ib,

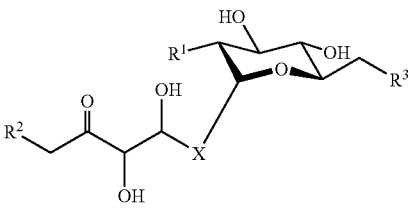

wherein:
X represents —O—, —OCH$_2$—, —CH$_2$—, —S—, —SCH$_2$—, —NH— or —NHCH$_2$—;
R$^1$ represents QR$^4$, wherein Q represent —O—, —NH—, —NH—(C=O)—, —O—(C=O), —NH—(C=O)—O— or —NH—(C=O)—NH—; and wherein R$^4$ represents a linear or branched alkyl or aryl group or a linear or branched aralkyl or alkaryl group;
R$^2$ is a phosphate, phosphonate, carboxylate, or sulphonate group; and
R$^3$ is OH or YR$^5$ wherein Y is —O—, —CH$_2$— or —NH— and R$^5$ is a linear or branched alkyl or aryl group or a linear or branched aralkyl or alkaryl group,
with a predetermined amount of P-selectin or said functional equivalent of P-selectin and
subsequently determining the amount of the same compound.

10. A method of treating or inhibiting a disease or condition involving activation and/or overexpression of P-selectin in a mammal inflicted with such a disease, the method comprising administering to the mammal an effective P-selectin inhibiting amount of a composition according to claim 8.

11. The compound according to claim 1, wherein X represents —$CH_2$—.

12. The compound according to claim 1, wherein Q represents —NH—(C=O)—.

13. The compound according to claim 1, wherein X represents —$OCH_2$— and Q represents —NH—(C=O)— or —NH—(C=O)—O—.

* * * * *